US00PP14063P39

(12) United States Plant Patent
Brljevich

(10) Patent No.: US PP14,063 P3
(45) Date of Patent: Aug. 12, 2003

(54) VARIETY OF CALLA LILY NAMED 'RED SOX'

(75) Inventor: Trevor Brljevich, Maungaturoto (NZ)

(73) Assignee: Puke Karoro Exotics Limited (NZ)

( * ) Notice: Subject to any disclaimer, the term of this patent is extended or adjusted under 35 U.S.C. 154(b) by 39 days.

(21) Appl. No.: 09/870,051

(22) Filed: May 30, 2001

(65) Prior Publication Data

US 2002/0184689 P1 Dec. 5, 2002

(51) Int. Cl.[7] ..... A01H 5/00
(52) U.S. Cl. ..... Plt./263
(58) Field of Search ..... Plt./263, 313

(56) References Cited

PUBLICATIONS

UPOV–ROM, 2001/04, Plant Variety Database, GTI Jouve Retrieval Software, 2 citations for 'Red Sox', 2001.*
Certificaat Inzake de Verlening van een Communautair Kwekersrecht, Community Plant Variety Office, ARA 147, New Zealand Grant of Plant Variety Rights, No. 1073.*

* cited by examiner

*Primary Examiner*—Howard J. Locker
(74) *Attorney, Agent, or Firm*—Webb Ziesenhiem Logsdon Orkin & Hanson, P.C.

(57) ABSTRACT

'Red Sox' is a new variety of calla lily having a large flower with a scarlet-red colored spathe and producing 1–4 flowers per tuber. The leaves are a spotted medium green color with a leathery texture.

1 Drawing Sheet

Botanical classification: *Zantedeschia sprengeri.*
Varietal denomination: 'Red Sox'.

BACKGROUND OF THE INVENTION

The present invention comprises a new and distinct cultivar of calla lily, botanically known as *Zantedeschia sprengeri* and hereinafter referred to by the cultivar name 'Red Sox'.

'Red Sox' was discovered in 1992 in a selection of seedling tubers of unknown parentage in Maungaturoto, New Zealand. The new cultivar has a larger and more scarlet red colored spathe than other red colored calla lilies and is taller than other red colored calla lilies known to the inventor.

The first act of asexual reproduction of the new cultivar was performed by tissue culture in 1994 in Albany, Auckland, New Zealand. The new cultivar retained its characteristics through successive propagations.

BRIEF DESCRIPTION OF THE DRAWINGS

The accompanying photographic drawing illustrates the new variety, with the color being as nearly true as is possible with color illustrations of this type.

DESCRIPTION OF THE PLANT

Figure 1:
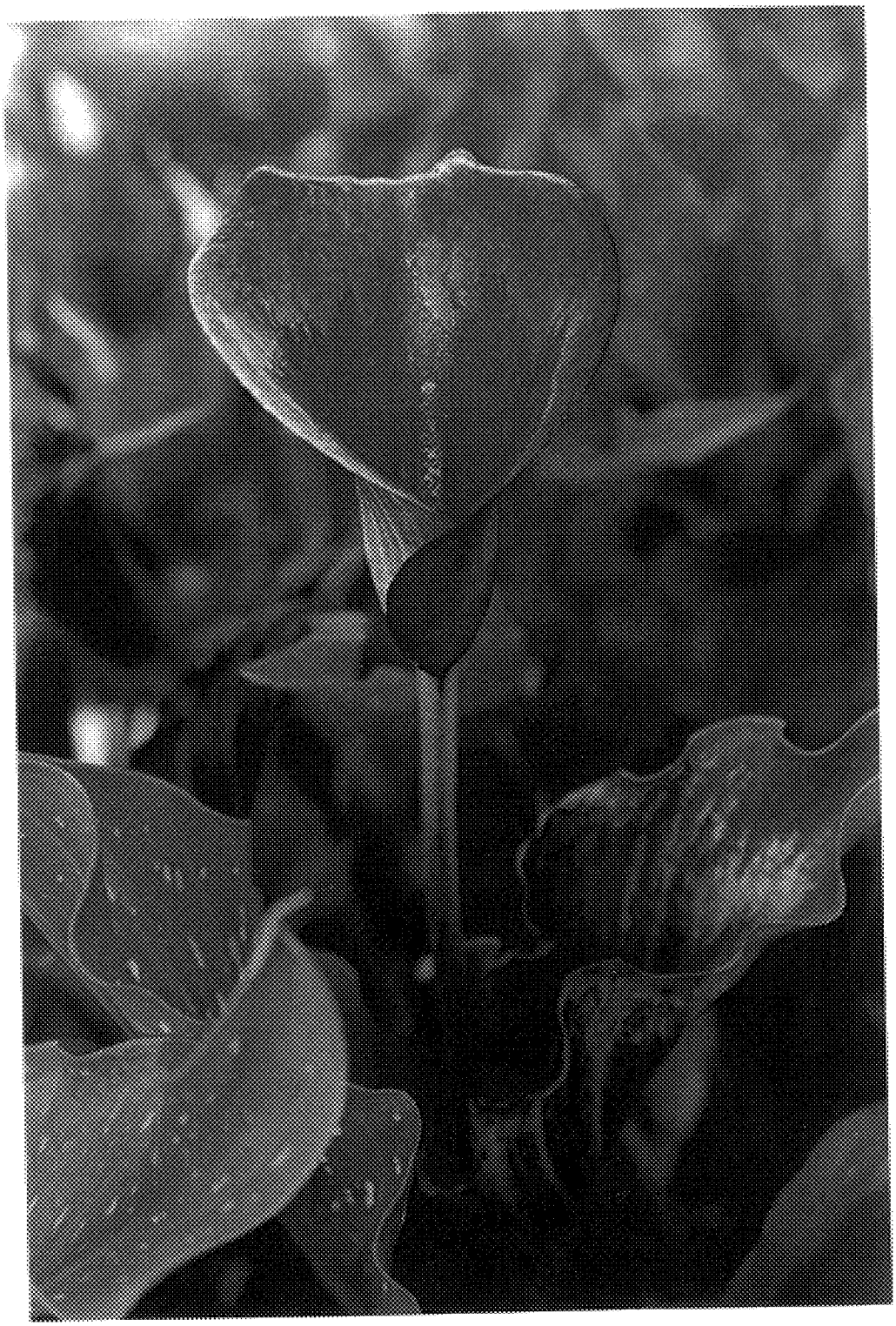
FIG. 1 is a photograph of a single bloom above the leaves. The photograph was taken in the morning with some sunlight reflection distorting the color in the widening area of the spathe.

The following observations, measurements and comparisons describe plants grown in Paparoa, New Zealand under conditions which approximate those generally used in horticultural practice. Color references are made to The R.H.S. Colour Chart of The Royal Horticultural Society of London, except where general color terms of ordinary significance are used.

THE PLANT

Size:
- *Height of the leaf canopy above the soil.*—40–90 cm.
- *Height of top of flower above the soil.*—50–100 cm.
- *Diameter.*—10–20 cm.
- *Form.*—Erect.

Number of flowers per tuber:
- *Tuber diameter* 3–4 cm.—1–2 flowers.
- *Tuber diameter* 4–5 cm.—1–3 flowers.
- *Tuber diameter* 5–6 cm.—2–4 flowers.

Branches:
- *Character.*—Strong; 2–3 per plant.
- *Color.*—Green Group 137C.

Leaves:
- *Size.*—Width: 9–14 cm. Length: 15–25 cm.
- *Shape.*—Lanceolate.
- *Number per plant.*—8–20.
- *Color.*—Upper surface: Green Group 137A with medium-heavy maculations following the direction of veination and which generally are transparent or are Red-Purple Group 59B when on base of mature leaves. Maculations are generally sized 5–10 mm long interspersed with some sized 1–2 mm long 250–400 maculations per mature leaf. Lower surface: Green Groups 137C and 137D. Margin: A very thin streak of Red-Purple Group 59B may be present on mature leaves.
- *Veins.*—Configuration: Pinnate. Color: Yellow-Green Group 150C to transparent. Surface quality: Leathery.

Petiole:
- *Length.*—25–65 cm.
- *Color.*—Green Group 143C with striations of Green Group 143A.

Roots:
- *Color.*—White.
- *Branching.*—Average amount.

Disease resistance: Moderately resistant.
Pest resistance: No unusual susceptibility to pests.

THE FLOWER

Spathe:

*Size.*—Length: 70–90 mm. Width: 60–80 mm.

*Color.*—Inner surface: Greyed-Purple Group 184A, and Greyed-Red Groups 182A and 180A shading towards the base to Yellow Group 4C at center. Outer surface: Greyed-Purple Group 184A and Greyed-Red Groups 182A and 180A with striping shading to Yellow Groups 13C and 10B; apex is Green Group 139A.

*Veins.*—Configuration: Parallel. Color: Greyed-Purple Group 184A, Greyed-Red Group 180A shading to Yellow Groups 10B and 4C at the base.

*Shape.*—Overall: Cup shaped. Tip: Apex pointed and reflexing. Base: Cylindrical and distally widening.

Spadix:

*Size.*—Length: 35–45 mm; 10–25 female reproductive organs located on lower 10–15 mm. Diameter: 0.5–0.8 mm.

*Color.*—Immature male reproductive organs: Yellow Groups 13A and 17A. Immature female reproductive organs: Green Group 145B with hint of Greyed-Red Group 180A speckling.

*Position relative to spathe.*—Upright.

Peduncle:

*Size.*—Length: 40–90 cm. Diameter: 0.8–0.12 mm.

*Color.*—Green Group 143C with striations of Green Group 143A and faint background coloring of Greyed-Red Group 180A.

*Flowering.*—Tubers planted in New Zealand begin to flower 85 days after planting and will continue to flower over a 40 day period.

*Blooming period.*—About 4–6 weeks; cut spathe lasts 5–14 days.

*Fragrance.*—None.

REPRODUCTIVE ORGANS

Location of female organs: Lower 40% of spadix.

Location of male organs: Upper 60% of spadix.

Perianth: Conspicuous.

Stamens: Not visible before pollen release.

Pistil:

*Length beyond perianth.*—About 0.5–1.0 mm.

*Shape.*—*Conical.*

I claim:

1. A new and distinct variety of calla lily plant named 'Red Sox' as described and illustrated.

* * * * *